(12) United States Patent
Mallett et al.

(10) Patent No.: US 8,062,876 B2
(45) Date of Patent: Nov. 22, 2011

(54) METHOD FOR ACTIVATING PRETHROMBIN-1

(75) Inventors: Robert W. Mallett, Ravensdale, WA (US); Christopher J. Stenland, Stanwood, WA (US); Jonathon C. Boone, Kenmore, WA (US); John W. Forstrom, Seattle, WA (US); Karen S. De Jongh, Seattle, WA (US)

(73) Assignee: Zymogenetics, Inc., Princeton, NJ (US)

( * ) Notice: Subject to any disclaimer, the term of this patent is extended or adjusted under 35 U.S.C. 154(b) by 793 days.

(21) Appl. No.: 12/097,027

(22) PCT Filed: Dec. 21, 2006

(86) PCT No.: PCT/US2006/049076
§ 371 (c)(1),
(2), (4) Date: Jun. 11, 2008

(87) PCT Pub. No.: WO2007/076033
PCT Pub. Date: Jul. 5, 2007

(65) Prior Publication Data
US 2008/0293122 A1      Nov. 27, 2008

(51) Int. Cl.
*C12N 9/74* (2006.01)
(52) U.S. Cl. ........................................... 435/214
(58) Field of Classification Search .................. None
See application file for complete search history.

(56) References Cited

FOREIGN PATENT DOCUMENTS
WO       03/070746       8/2003

OTHER PUBLICATIONS

Rao et al., *Blood* 102(4):13471354, 2003.
Joseph et al., *Blood* 94(2):621-631, 1999.
Pierre et al., *Mol. Biol. Evol.* 22(9):1853-1864, 2005.
Welton et al., *Toxicon* 46:328-336, 2005.
Rao et al., *Thromb Haemost* 88:611-619, 2002.
Rao et al.,*Thromb Haemost* 92:509-521, 2004.
Kini, *Toxicon* 45:1133-1145, 2005.
Speijer et al., *J. Biol. Chem.* 261(28):13258-13267, 1986.
Takashi Morita et al., "Prothrombin Activator from *Echis carinatus* Venom"; Method in Enzymology, vol. 80, pp. 303-311.
Ramona J. Petrovan et al., Purification and Characterization of Multisquamase, the Prothrombin Activator Present in *Echis multisquamatus* Venom; Thrombosis Research 88 (1997), pp. 309-316.
Australian Office Action mailed May 13, 2009.

*Primary Examiner* — Tekchand Saidha
*Assistant Examiner* — Md. Younus Meah
(74) *Attorney, Agent, or Firm* — Nixon Peabody, LLP; Mary S. Webster

(57) ABSTRACT

Methods for converting prethrombin-1 to thrombin are disclosed. An aqueous solution of prethrombin-1 is applied to oscutarin-C immobilized on a solid support so as to provide from 500 mg to 4000 mg of prethrombin-1 per mL of the solid support and a contact time between the prethrombin-1 and the oscutarin-C of from 1.8 to 3.5 minutes. The resulting active thrombin may be captured on an ion exchange chromatography medium or an affinity chromatography medium.

19 Claims, 10 Drawing Sheets

METHOD FOR ACTIVATING PRETHROMBIN-1

The present application claims priority to PCT/US2006/049076, filed on Dec. 21, 2006.

BACKGROUND OF THE INVENTION

The penultimate step of the coagulation cascade is the Factor Xa-complex-catalyzed conversion of the zymogen prothrombin to the active enzyme thrombin. Prothrombin is a single-chain, vitamin K-dependent glycoprotein that is synthesized in the liver. It contains a gla domain, two kringle regions, an A chain, and a serine protease domain (B chain). Conversion to thrombin requires that prothrombin be cleaved in two places, removing the gla domain and kringle regions and cleaving between the A and B chains to produce the active protease, termed "α-thrombin."

Thrombin is used therapeutically to promote hemostasis in surgery and as a component of tissue adhesives and sealants. Human and bovine thrombins, both derived from plasma, are currently approved for therapeutic use.

It would be advantageous to obtain thrombin from a recombinant source to avoid the potential for contamination that is inherent in plasma-derived products. Bovine thrombin has been associated with hemostatic abnormalities resulting from immunogenicity of the bovine thrombin itself and/or contaminant proteins (Ortel et al., *Ann. Surg.* 233(1):88-96, 2001; Lawson et al., *Ann. Thorac. Surg.* 79(3):1037-1038, 2005) and carries a "black box" warning cautioning against repeat use in patients who have developed antibodies to bovine thrombin. However, production of recombinant prothrombin has proven problematic and yields have remained low.

As an alternative to purification from plasma, thrombin can be prepared from a recombinant prethrombin (e.g., prethrombin-1) as disclosed in U.S. Pat. No. 5,476,777. Prethrombin-1 is an inactive thrombin precursor that does not contain the gla domain or the first kringle region of prothrombin, which can be produced by expression of a truncated prothrombin DNA in recombinant cells. Active thrombin is produced from prethrombin-1 by treatment with any of several activating proteases, including prothrombin activators obtained from snake venom. See, for example, Speijer et al., *J. Biol. Chem.* 261:13258-13267, 1986; Masci et al., *Biochemistry International* 17:825-835, 1988; and Morita et al., *Meth. Enzym.* 80:303-311, 1980.

Activation of prethrombin-1 to thrombin is complicated by the proteolytic activity of α-thrombin on prethrombin. This activity, which can reduce overall yield of α-thrombin, can be enhanced by conditions needed to stabilize the protein. There remains a need in the art for methods of efficiently activating prethrombin-1 to α-thrombin.

DESCRIPTION OF THE INVENTION

The present invention provides methods for converting prethrombin-1 to thrombin. The methods of the invention comprise the steps of (a) providing prethrombin-1 at a concentration of 0.1 mg/mL to 10 mg/mL in an aqueous solution of 30 mM to 110 mM NaCl at pH 6.4-8.0, (b) providing oscutarin-C immobilized on a solid support, and (c) applying the aqueous solution to the immobilized oscutarin-C so as to provide from 500 mg to 4000 mg of prethrombin-1 per mL of the solid support and a contact time between the prethrombin-1 and the oscutarin-C of from 1.8 to 3.5 minutes, inclusive, whereby the prethrombin-1 is cleaved to produce thrombin, and a thrombin-containing solution is obtained. Within one embodiment of the invention, the aqueous solution of prethrombin-1 is at pH=7.4. Within another embodiment of the invention, the prethrombin-1 is human prethrombin-1. Within further embodiments of the invention, the oscutarin-C is immobilized on the solid support at a concentration of from 0.1 to 20 mg of oscutarin-C per mL of support. Within related embodiments, the oscutarin-C is immobilized on the solid support at a concentration of from 0.1 to 5.0 mg of oscutarin-C per mL of support. Within another embodiment of the invention, the solid support comprises a cross-linked agarose matrix. Within an additional embodiment, the NaCl concentration in the aqueous solution of prethrombin-1 is 70 mM. Within other embodiments, the methods of the invention are carried out at a temperature of from 17° C. to 45° C., a temperature of from 20° C. to 37° C., a temperature of from 20° C. to 30° C., or a temperature of 25° C.

Within certain embodiments of the invention, the methods further comprise the steps of (d) applying the thrombin-containing solution to a capture medium selected from the group consisting of an ion exchange chromatography medium and an affinity chromatography medium, whereby the thrombin is bound to the capture medium, (e) washing the bound thrombin, and (f) recovering the bound thrombin from the capture medium. Within certain embodiments, the capture medium is an affinity chromatography medium, such as a medium that comprises para-aminobenzamidine (PABA) immobilized on a solid support. Within a related embodiment, the capture medium comprises immobilized PABA, and the recovering step comprises washing the immobilized PABA with NaCl and isopropanol at concentrations sufficient to elute the bound thrombin.

These and other aspects of the invention will become evident upon reference to the following detailed description of the invention and the attached drawings. In the drawings.

Figure 3:
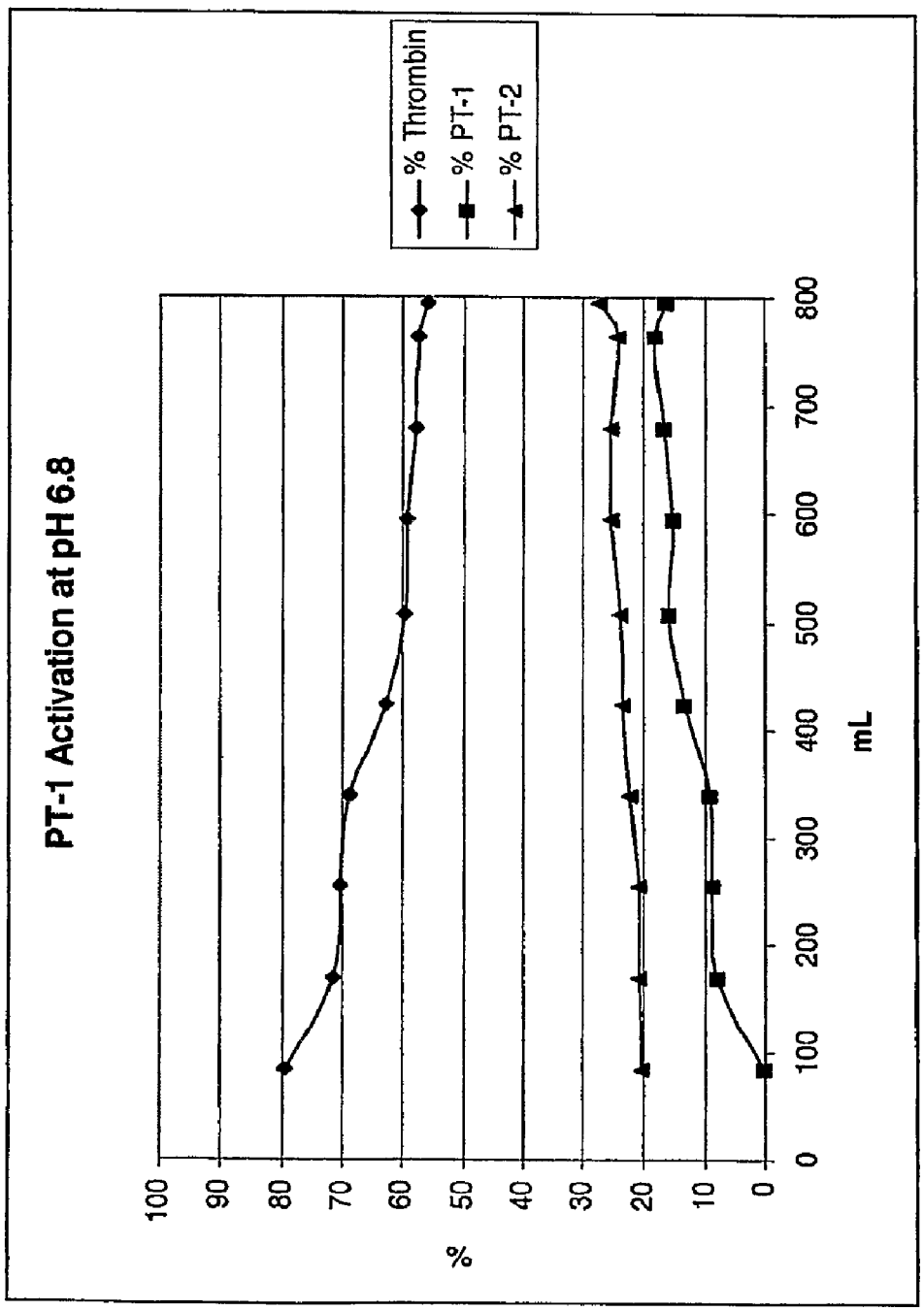
Figure 4:
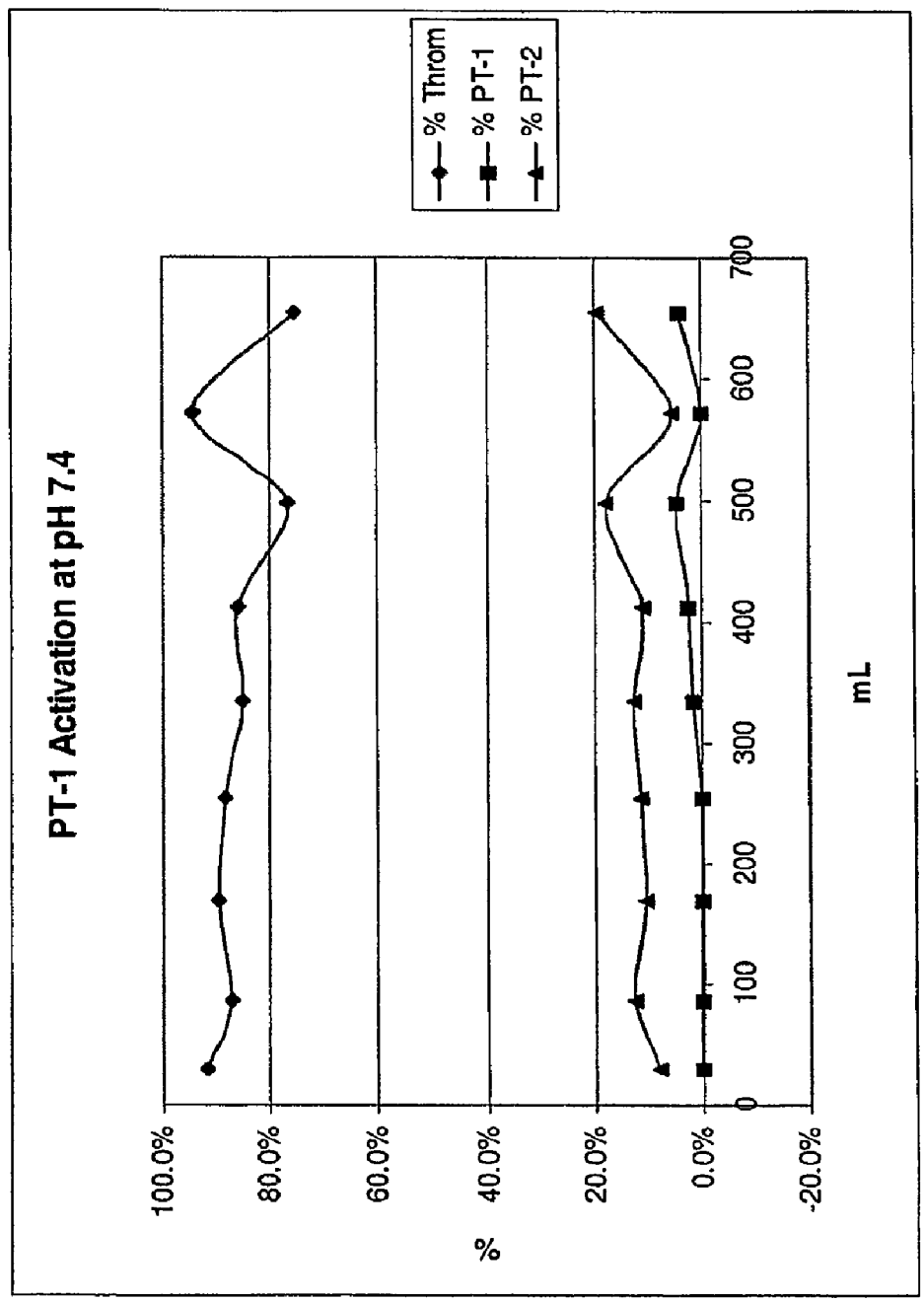
Figure 5:
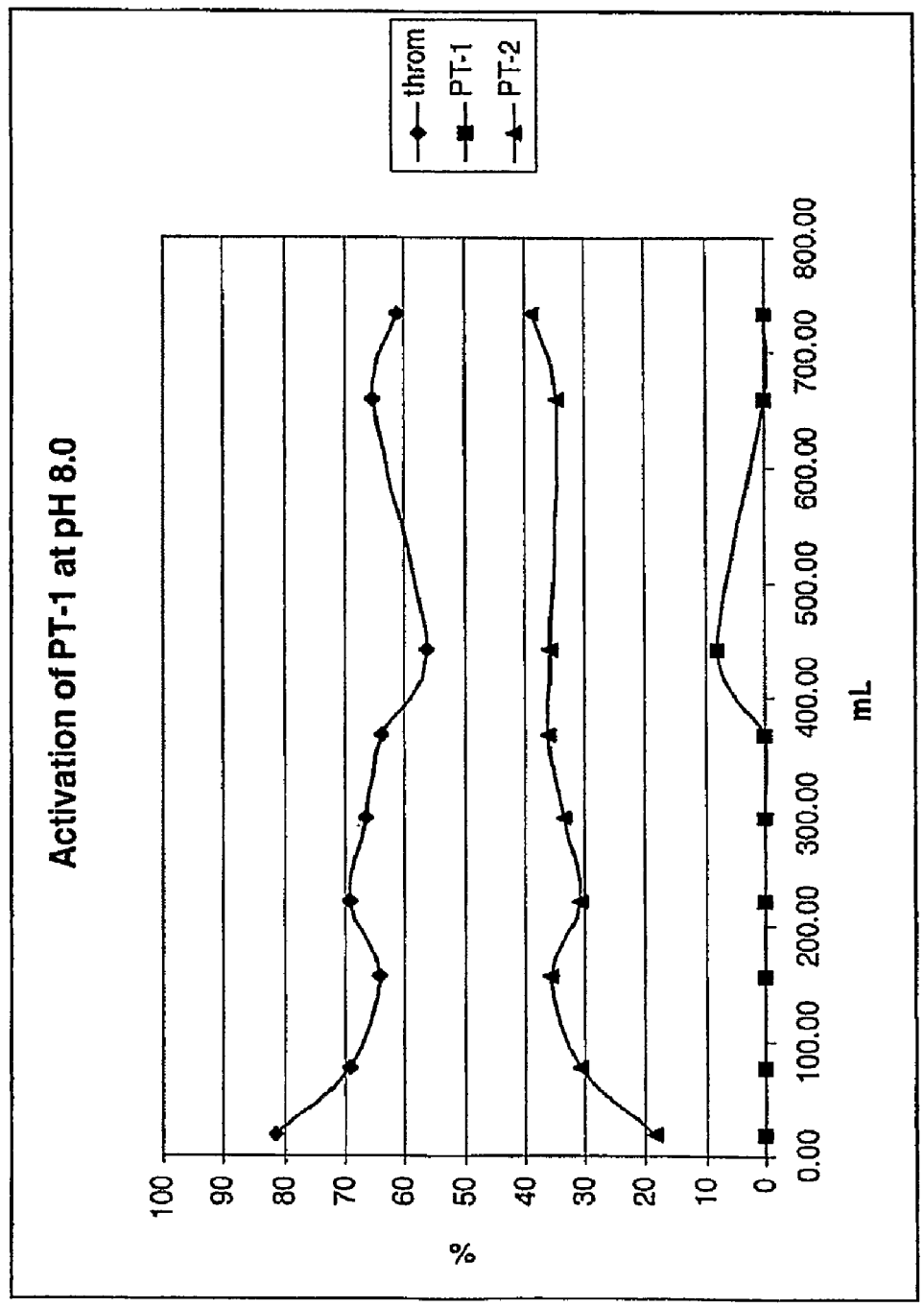

FIGS. 3, 4, and 5 illustrate the effects of pH on activation of prethrombin-1 to thrombin.

Figure 6:
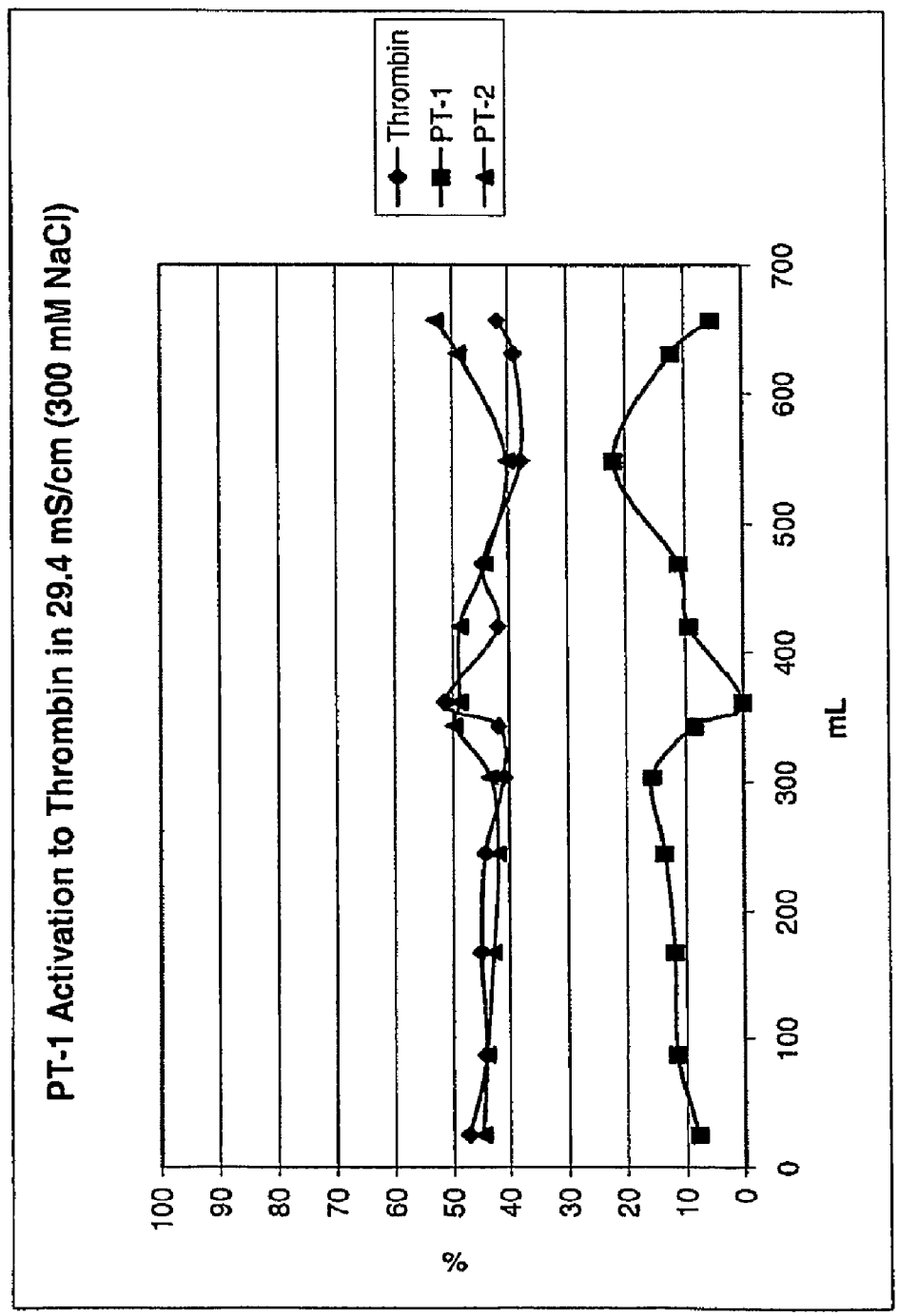
Figure 7:
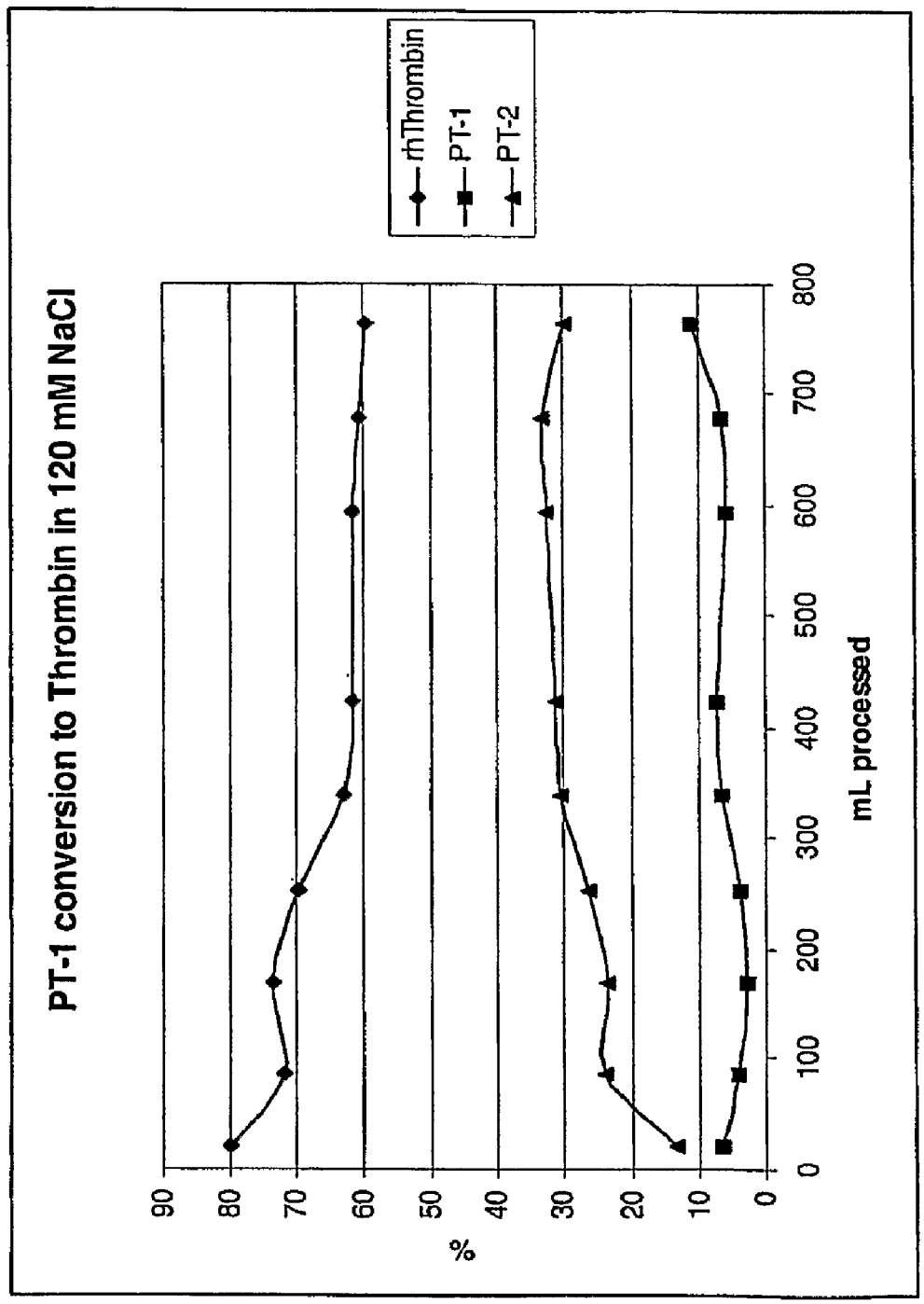
Figure 8:
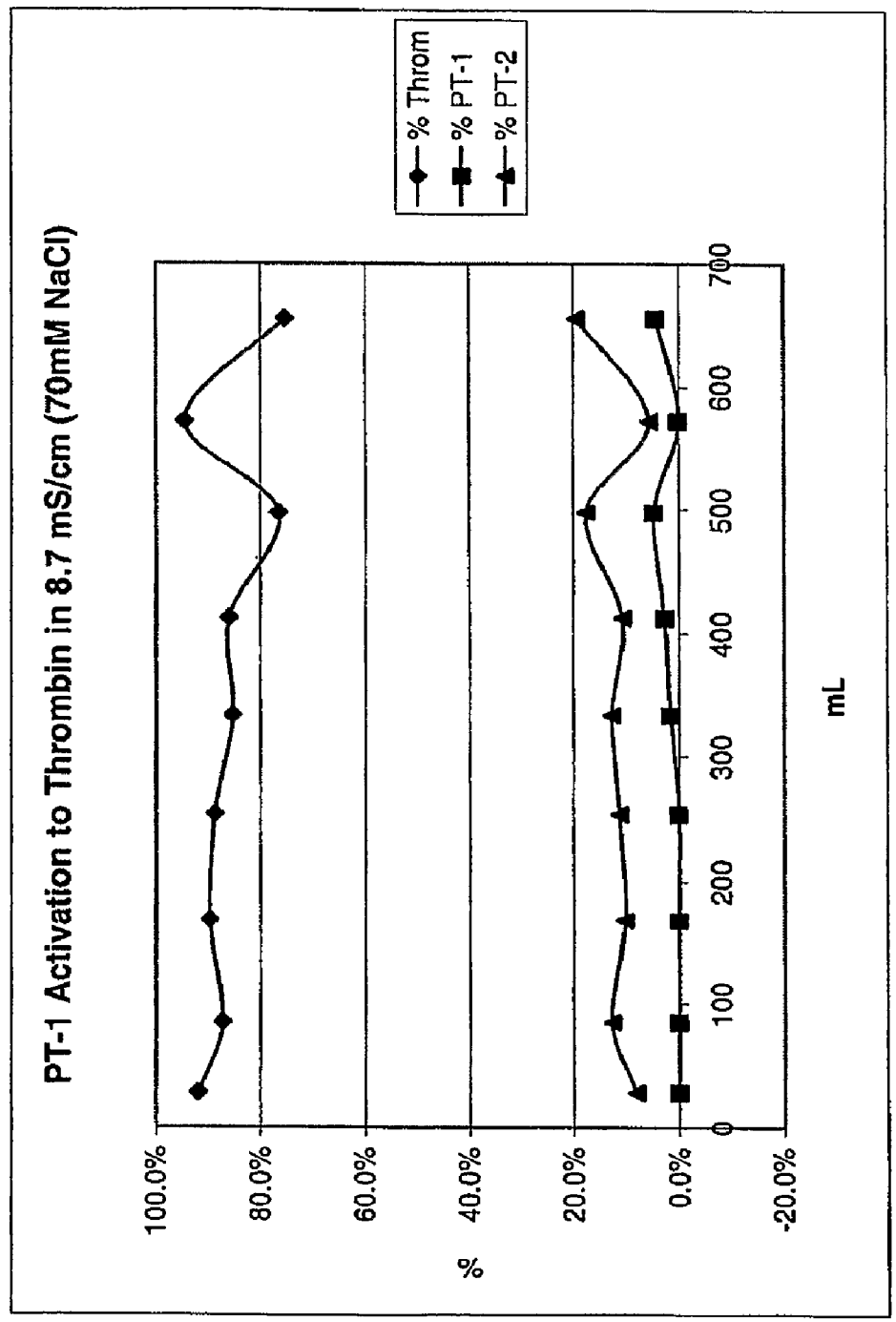

FIGS. 6, 7, and 8 illustrate the effects of NaCl concentration of the activation of prethrombin-1 to thrombin.

Figure 9:
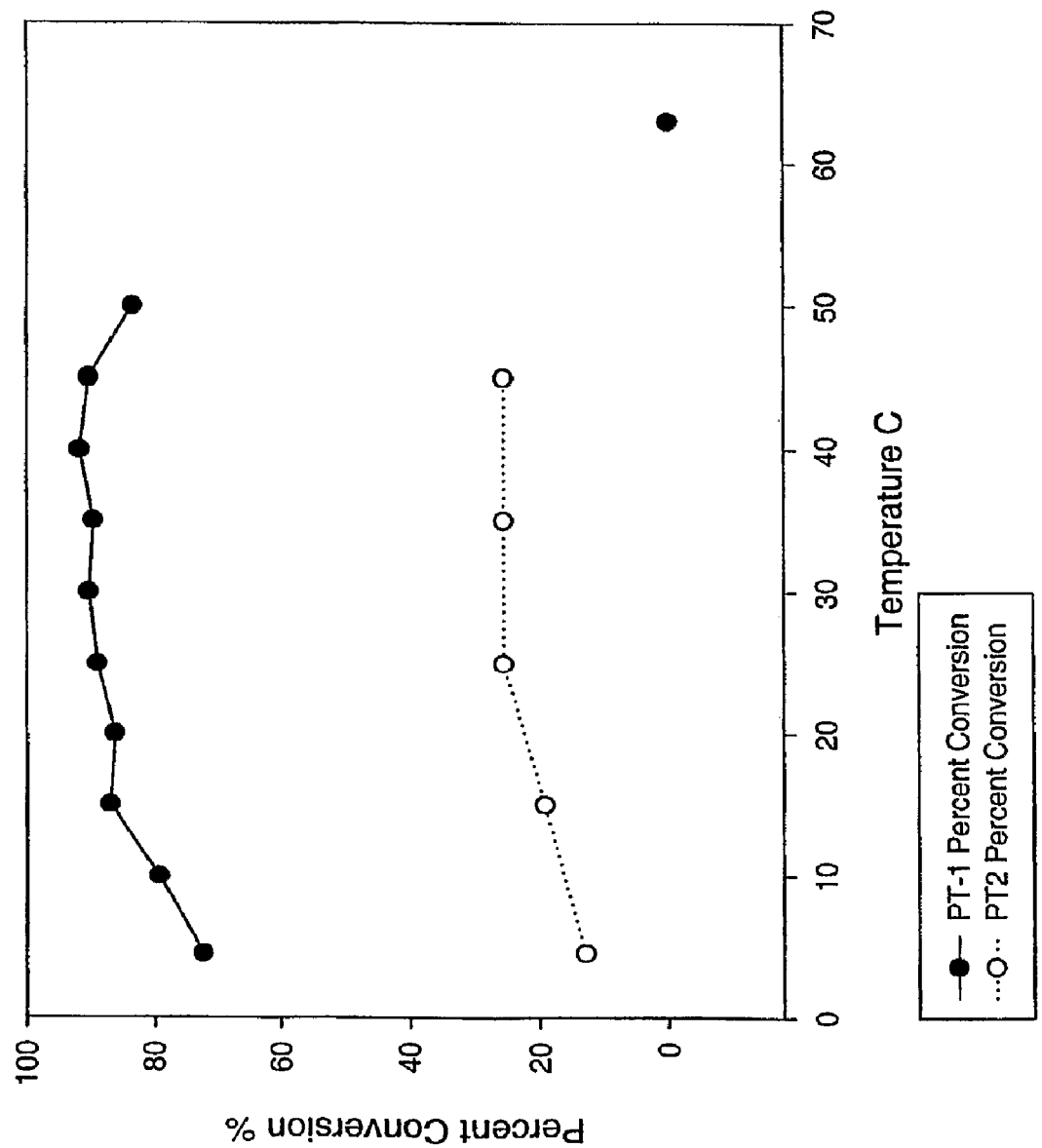

FIG. 9 illustrates the effect of temperature on the conversion of PT-1 and PT-2 to thrombin.

Figure 10:
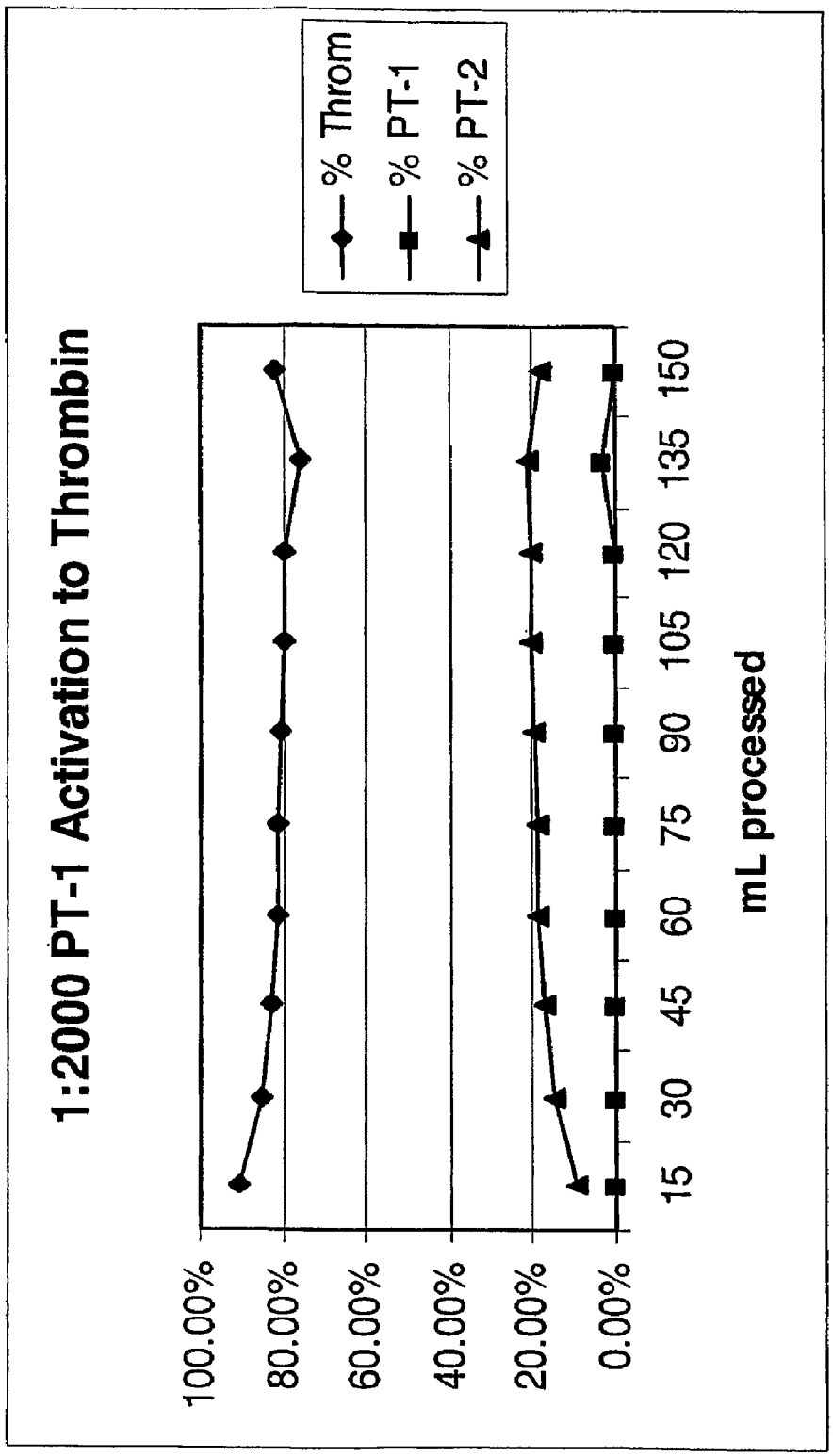

FIG. 10 shows the relative amounts of thrombin, PT-1, and PT-2 in an activation run using a 4.0 mg/mL PT-1 load and a contact time of 2.5 minutes.

As used herein, "thrombin" denotes the activated enzyme, also known as α-thrombin, which results from the proteolytic cleavage of prothrombin (factor II). The term "thrombin" is used herein to denote this protein regardless of its origin. Human thrombin is a 295 amino acid protein composed of two polypeptide chains joined by a disulfide bond. Both human and non-human thrombins can be used within the present invention. Thrombin is used medically as a hemostatic agent and as a component of tissue adhesives.

"Prethrombin-1" is a protein that results from the removal of the gla and first kringle domains (collectively known as prothrombin fragment 1) from prothrombin. Prethrombin-1 can be produced by cleavage of prothrombin with thrombin or directly by recombinant production. Prethrombin-1 can be activated to thrombin by further proteolytic cleavage.

Numerical ranges recited herein are inclusive of their endpoints.

All references cited herein are incorporated by reference in their entirety.

The present invention provides methods for activating the thrombin precursor prethrombin-1 (PT-1) to the active enzyme thrombin. Although, for purposes of illustration, the invention is described in terms of recombinant human PT-1, the invention also includes the activation of non-human and non-recombinant forms of prethrombin-1. Thus, the invention includes, without limitation, methods for activating human and non-human (e.g., bovine) plasma-derived PT-1 and recombinant PT-1.

Within the present invention, activation of prethrombin-1 (PT-1) to thrombin is achieved enzymatically by hydrolysis of the PT-1 polypeptide backbone at two specific sites. The enzyme used to catalyze this conversion is derived from the venom of the Coastal Taipan snake (*Oxyuranus scutellatus*). A complex serine protease (Oscutarin-C) purified from the crude venom is able to mimic the functions of Factors Va and Xa that are necessary for activation of prothrombin to thrombin in situ.

Within one embodiment of the invention, the activated thrombin is captured by affinity chromatography by passing the thrombin-containing eluant of the activator column over a column of immobilized para-aminobenzamidine (PABA). The PABA is immobilized on a polymeric bead support. Suitable supports include polymers of methacrylate, acrylamide, agarose, and the like, functionalized with chemistries such as epoxy, active esters, thiol, and cyanogen bromide chemistries. A variety of supports and activation chemistries are known in the art. See, for example, Hermanson et al., Immobilized Affinity Ligand Techniques, Academic Press, New York, 1992. Contaminants, including prothrombin fragment 2 and host cell proteins, can be eluted from the column using 70 mM to 500 mM NaCl, 5% to 20% isopropanol by volume, or a combination of NaCl and isopropanol. Within one embodiment of the invention, contaminants are eluted using 264 mM NaCl in 7.1% (v/v) isopropanol, buffered to approximately neutral pH. The activated thrombin can then be eluted using increased concentrations of NaCl (300 mM to 500 mM, preferably about 500 mM), isopropanol (10% to 20% by volume, preferably about 15.7% by volume), or a combination of NaCl and isopropanol at these concentrations. Within one embodiment, the thrombin is eluted using 500 mM NaCl in 15.7% (v/v) isopropanol. Such a combination of NaCl and isopropanol confers stability to thrombin following elution off the PABA column. Elutions can be carried out using a concentration gradient or in a step-wise manner. Although thrombin and fragment 2 can be eluted using the same concentration ranges, with fragment 2 eluting first, the use of lower concentrations of NaCl and/or isopropanol for the elution of fragment 2 and higher concentrations for elution of thrombin results in smaller elution volumes and improved separation.

Thrombin eluted from the activator column can also be captured by other chromatographic methods, such as ion exchange chromatography, immunoaffinity chromatography, or affinity chromatography (e.g., heparin affinity chromatography).

Oscutarin-C (also referred to herein as "prothrombin activator" or "PTA") is a tetramer consisting of two Factor Xa-analogous subunits and two Factor Va-analogous subunits. While not wishing to be bound by theory, it is believed that the Factor Xa-type subunits are responsible for the catalytic activity of the complex, and the Factor Va-type subunits are necessary to stabilize the PT-1 molecule in the appropriate configuration to enable activation. See, Speijer et. al. (ibid.). To use the purified PTA as an activation agent to convert PT-1 to thrombin, the enzyme is immobilized on a solid support. Suitable supports include any chromatographic resin activated with chemistries reactive with amine, sulfhydryl, carboxyl, hydroxyl, or carbohydrate moieties on the PTA molecule, whereby such reaction results in a covalent linkage of the PTA with the resin. Examples of such supports include agarose, cellulose, silica, and synthetic supports such as resins prepared from acrylamide, polystyrene, and methacrylate derivatives.

The supporting resin is loaded with Oscutarin-C at a ratio of from 0.1 mg to 20 mg of activator per mL of settled resin. As will be appreciated by those skilled in the art, capacities of individual resins may vary somewhat, and actual conditions will be established by routine process optimization. In general, resin loading densities as high as 10 to 20 mg of activator per mL of resin will be achievable with conventional resin supports and may allow for higher prethrombin-1 to resin activation ratios (>2.0 g/mL of resin) or shorter activation times. A cross-linked agarose resin loaded with 1.0 mg PTA per mL of resin was found to be sufficient to activate at least 2.0 grams of PT-1 to thrombin per mL of coupled resin, with an overall molar yield of thrombin in excess of 70% under optimal conditions. This ratio of PTA to resin has the potential of activating greater than 4 grams of PT-1 per mL of resin achieving only a slightly lower conversion to thrombin.

Immobilization conditions were optimized using cyanogen bromide-activated, cross-linked agarose resin (utilizing SEPHAROSE FAST FLOW from Amersham BioSciences). Standard immobilization conditions (as specified by the manufacturer) were initially used. However, PTA was found to be susceptible to inactivation by low pH washes, resulting in irreversible inactivation when washing below pH 4.5, and the instability of the PTA molecule was exacerbated by addition of 0.5 M NaCl to the reaction mixture. Washing at pH 5.0 was found to be sufficient to remove any impurities while preserving resin activity. Thus, washing at a pH below 4.5 should be avoided. The enzyme was not affected by washing at higher pH levels (to at least 8.3). Treatment of the resin with low pH buffer (e.g., pH 4.0) may be tolerated for short time intervals while maintaining resin activity. However, washing the resin with buffers below pH 4.5 will inactivate the resin in a time-dependent manner. The lower the pH, the less time is required for loss of activity.

The PTA resin can be stored under slightly acidic conditions. From a series of optimization experiments it was determined that the stability of the resin is maximum at pH 6.0 in sodium phosphate buffer containing 0.02% sodium azide as a bacteriostatic agent. The resin is only slightly less stable in 20% EtOH at pH 6.0.

Several parameters influence the activation efficiency of the PTA resin. Among these are pH, conductivity, PT-1 contact time, PT-1 concentration, and temperature. Although pH is an important parameter in determining the reaction equilibrium (PT-1 conversion to PT-2), the optimum pH for the conversion of PT-1 to thrombin is broad, between pH 6.8 and pH 8.0. The maximum affinity of serine proteases for p-aminobenzamidine (PABA) is around pH 8.0, therefore it is desirable to maintain the pH of the conversion reaction close to pH 8.0. Although increasing concentrations of NaCl inhibited the activation reaction, some NaCl is included in the reaction buffer to maintain stability of PT-1 in solution. Experimental evidence showed that there is a significant drop in PT-1 to thrombin conversion when the load contained 0.3 M NaCl and that decreasing concentrations of NaCl resulted in higher PT-1 to thrombin conversion ratios. Through a series of experiments it was determined that 70 mM NaCl provided a good combination of PT-1 stability and activation efficiency.

Within the present invention, a NaCl concentration from 30 mM to 110 mM can be utilized without incurring unacceptable losses. Activation efficiency has been found to increase with temperature; higher conversion rates were obtained at higher temperatures (see FIG. 9). Large-scale activation at 25° provides acceptable activation efficiency, although temperatures as high as 45° C. may be employed. However, lower temperatures may provide a longer useful life of the activator.

Figure 1:
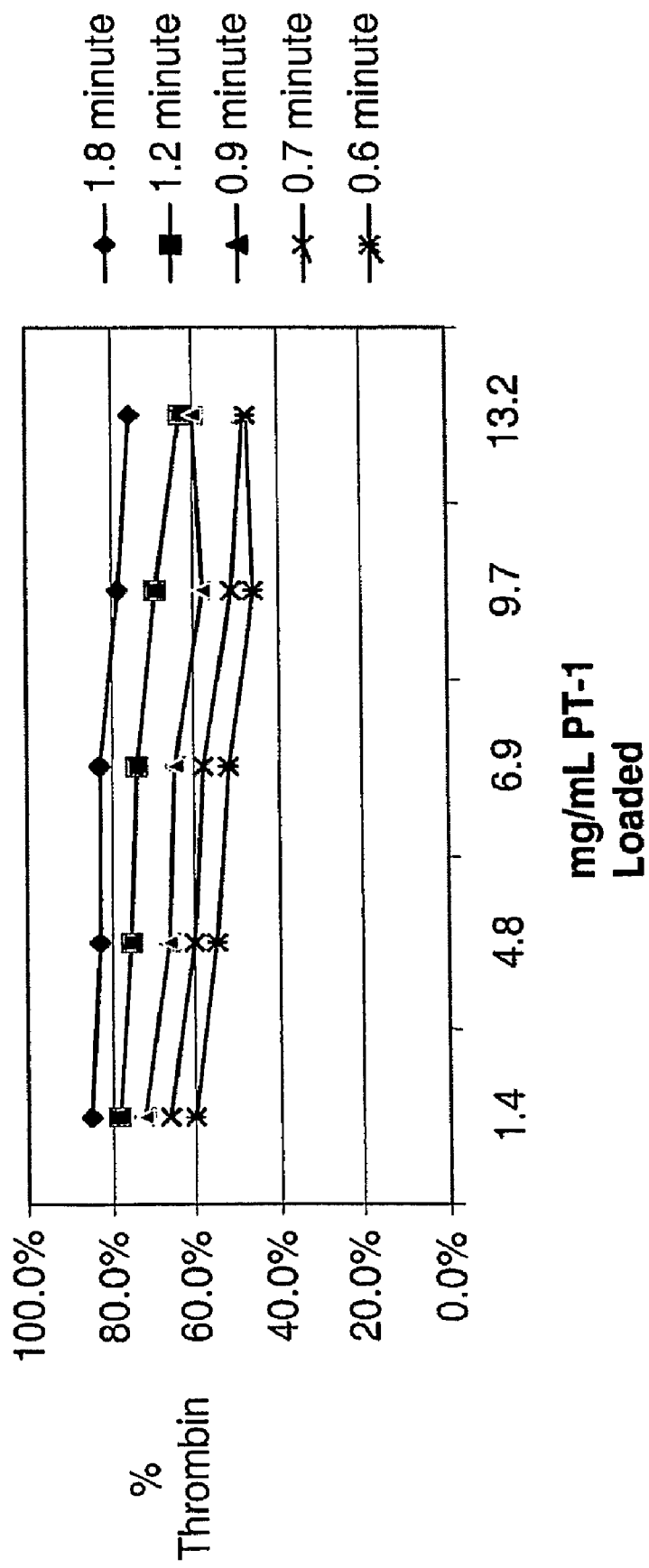
FIG. 1 illustrates the effects on activation efficiency of varying prethrombin-1 concentration and activator contact time.

PT-1 residence time on the activator column greatly influences conversion efficiency. Shorter contact times (as may be obtained through higher flow rates) result in poorer conversion of PT-1 to thrombin. The relationship between PT-1 concentration and PTA contact time from 0.6 to 1.8 minute is shown in FIG. 1. At higher PT-1 concentrations (between 4 and 6 mg/mL) a contact time of 2.5 minutes results in good conversion. FIG. 10 shows the relative amounts of thrombin, PT-1, and PT-2 in an activation run using a 4.0 mg/mL PT-1 load and a contact time of 2.5 minutes. Thus, as the PT-1 concentration increases, the contact time may be increased to maintain a high rate of PT-1 to thrombin conversion. By manipulating the PT-1 load concentration and the PT-1-PTA resin contact time, one skilled in the art can develop a matrix of suitable reaction combinations. For example, the process parameters shown in Table 1 have been found to provide suitable conversion efficiencies.

TABLE 1

| PT-1 Concentration | Contact Time |
|---|---|
| 1 mg/mL | 1.8 min. |
| 5 mg/mL | 2.5 min. |
| 10 mg/mL | 3.5 min. |

Surprisingly, the concentration of PT-1 in the load solution did not greatly influence the efficiency of the conversion up to about 9.0 mg/mL. There was some loss in efficiency at higher PT-1 concentrations, but the conversion efficiency could be recovered by slightly increasing the contact time as shown in FIG. 1.

Figure 2:
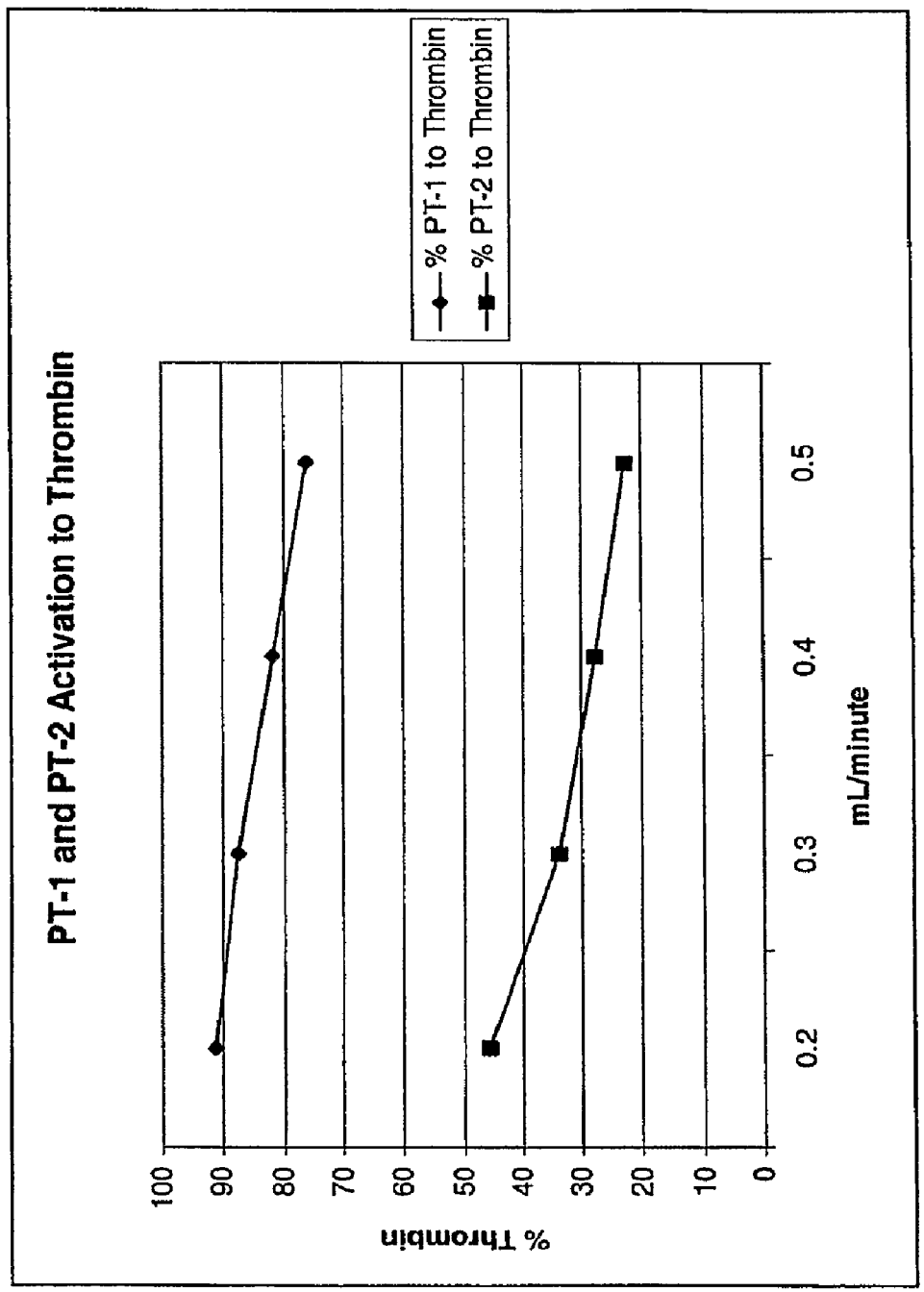
FIG. 2 shows the rates of conversion of prethrombin-1 (PT-1) and prethrombin-2 (PT-2) to thrombin as a function of flow rate through the activator column.

Before and during the PT-1 activation process a portion of the PT-1 may be partially hydrolyzed by thrombin or endogenous proteases. The partially hydrolyzed form is called prethrombin-2 (PT-2) and lacks proteolytic activity. The PT-2 referred to here may exist in two forms varying in size by 13 amino acids. It is possible to convert PT-2 to thrombin via the Oscutarin-C activation pathway, but the activation kinetics are slower than those observed for PT-1 (FIG. 2). Because PT-2 conversion to thrombin is slower than the conversion of PT-1, it is desirable to limit the production of PT-2 in the reaction mixture. When working with recombinant cell cultures, harvesting the cell culture at higher cell viability (>50%) reduces PT-2 production. Increases in PT-2 in low viability cell culture are believed to be due to an increase in the level of endogenously produced cell culture proteases that cause PT-1 conversion to PT-2 after the cell viability drops below 50%.

Following recovery of activated thrombin, further purification can be achieved using one or more conventional protein fractionation techniques. Suitable methods include, for example, ion exchange chromatography, buffer exchange, filtration (including nanofiltration to remove viruses), and concentration.

For use as a therapeutic agent, the purified thrombin is formulated with a physiologically acceptable vehicle. Preferred formulations include weakly buffered, aqueous solutions containing sucrose, mannitol, sodium chloride, a surfactant or high molecular weight polyethylene glycol (HMW-PEG), and, optionally, calcium chloride. Typical concentration ranges of these components are shown in Table 2. Concentrations expressed as percent are on a weight-to-volume basis.

TABLE 2

| thrombin | 0.01-5.0 mg/mL |
|---|---|
| sucrose | 2%-4% |
| mannitol | 3.5%-5% |
| NaCl | 50-300 mM |
| surfactant or HMW-PEG | 0.03%-1% |
| $CaCl_2$ | 0-5 mM |
| pH | 5.7-7.4 |

For long-term storage, the aqueous solution is aliquoted into sterile vials, ampoules, or other containers and lyophilized according to procedures known in the art.

For use, the lyophilized thrombin composition is reconstituted with a suitable diluent to the desired concentration, generally from about 100 NIH U/ml to about 5,000 NIH U/ml, typically about 1,000 NIH U/ml, although the actual concentration will be determined by the physician according to the needs of the individual patient. The thrombin can be applied to bleeding tissue to achieve hemostasis, often in combination with an absorbable gelatin sponge or as a spray. The thrombin can also be used as a component of a tissue adhesive or fibrin glue. These and other uses of thrombin are known in the art.

The invention is further illustrated by the following non-limiting examples.

EXAMPLES

Example 1

Recombinant prethrombin-1 was produced in CHO DG44 cells transformed with the THR101 expression vector disclosed in U.S. Pat. No. 5,527,692. The cells were cultured in a bioreactor in perfusion mode. Conditioned culture medium was harvested and clarified through a graduated series of depth filters and finally by ultrafiltration/diafiltration through a 0.2 μm PES (polyether sulfone) bilayer filter. A tangential flow ultrafiltration system configured with 30 kDa nominal molecular weight limit polyethersulfone membranes (PELLICON BIOMAX; Millipore Corp, Billerica, Mass.) was used to concentrate the clarified medium 10-fold. The concentrated medium was then continuously diafiltered with six diafiltration volumes of equilibration buffer (20 mM Tris, 120 mM NaCl, pH 9.1±0.1) to a concentration of 9.0 g/L prethrombin-1.

Viral inactivation of the prethrombin-1 was achieved by detergent treatment. A 10% (w/v) solution of 4-(1,1,3,3-Tetramethylbutyl)phenyl-polyethylene glycol (TRITON X-100) was added to the concentrated PT-1 solution to a final concentration of 0.5% (w/v). The solution was mixed and held for four hours at 12° C.±2° C. The solution was then cooled to below 8° C.

Contaminating prethrombin-2 and process impurities were removed by anion exchange chromatography. The detergent-treated solution was warmed to 16-22° C. and filtered to remove precipitates. The filtrate was loaded onto an 80 cm diameter×20 cm long column of derivatized agarose resin (Q SEPHAROSE XL; GE Healthcare) that had been equilibrated with 20 mM Tris, 120 mM NaCl, pH 9.1. The column was then washed with 10 column volumes of the same buffer, followed by 10 column volumes of 20 mM Tris, 142 mM NaCl, pH 8.8. The protein was then eluted with 5 column volumes of 20 mM Tris, 300 mM NaCl, pH 7.3. All column flows were at a linear velocity of 150 cm/hr. The eluate was monitored by absorbance ($A_{280}$), and the peak was collected and chilled to below 8° C.

The PT-1 solution was then concentrated by ultrafiltration through 30 kDa nominal molecular weight limit polyethersulfone membrane filters in a tangential flow filtration device (PELLICON BIOMAX; Millipore Corporation, Billerica, Mass.) to a concentration of 20±3 g/L. The concentrate was then filtered through 0.2 μm filters and frozen at −80° C.

The PT-1 was activated using immobilized oscutarin-C, and the thrombin was captured on a column of para-aminobenzamidine (PABA). The activator was immobilized through reactive amines present on the surface of the PTA molecule onto cyanogen bromide-activated agarose beads (SEPHAROSE FF; GE Healthcare) according to the manufacturer's direction, but with a pH 5.0 wash. After immobilization, the resin was packed in a 5 cm ID×10 cm bed height column (column volume=200 mL) in PTA equilibration buffer (20 mM Tris, 70 mM NaCl, pH 7.3). The PTA column was directly coupled to a 60 cm ID by 20 cm bed height (57 L) column of PABA resin (obtained from ProMetic Biosciences, Wayne, N.J.). The PABA resin was packed into the column, sanitized with 0.5 M NaOH, then neutralized with 100 mM Tris, pH 7.5, and stored in 25 mM sodium phosphate, 20% isopropanol, pH 7.0. The PTA and PABA columns were equilibrated with five column volumes of 20 mM Tris, 70 mM NaCl, pH 7.3 prior to coupling.

To activate the PT-1, frozen PT-1 concentrate (400 g PT-1) was thawed and diluted to a conductivity of 9.2±0.2 mS/cm with 20 mM Tris, pH 7.3, then further diluted to a concentration of 5 mg/ml PT-1 with 20 mM Tris, 70 mM NaCl, pH 7.3. The pH of the solution was then adjusted to 7.4±0.1 with 1.5 M sodium phosphate, pH 6.0, and the solution was filtered through a 0.2 μm filter. The filtered solution was then applied to the PTA column using a flow rate designed to allow a contact time of 2.5 minutes in the PTA column (80 mL/min). After completion of loading the PTA column was washed with at least five column volumes of equilibration buffer at the loading flow rate. The columns were then disconnected to allow elution of thrombin from the PABA column. Activation and capture were done at 25° C. and 17° C., respectively.

Thrombin was eluted from the PABA column under conditions that separated prothrombin fragment 2 (F2) and contaminating host cell proteins from thrombin. All steps were carried out at a flow rate of 38 cm/hr in the same direction that the column was loaded. The column was washed with at least 5 column volumes of buffer A (equilibration buffer; 20 mM Tris, 70 mM NaCl, pH 7.3). F2 was eluted with a 3-column-volume intermediate wash using 20 mM Tris containing 264 mM NaCl and 7.1% isopropanol. Elution of thrombin was done using 20 mM tris buffer and increasing the NaCl and iso-propanol concentrations to 500 mM and 15.7%, respectively. Production collection was done based on $A_{280}$ absorbance.

The activated thrombin was further purified using cation exchange chromatography. The PABA eluate was diluted with 10 mM histidine, pH 6.3, to a conductivity of not more than 13 mS/cm. The thrombin solution was then applied to a 45 cm diameter×12 cm long column (bed volume 19 liters) of sulfopropyl agarose resin (SP SEPHAROSE Fast Flow; GE Healthcare) that had been equilibrated with 10 mM histidine, 50 mM NaCl, pH 6.3. After loading, the column was washed with three column volumes of the same buffer. Thrombin was eluted with 10 mM histidine, 400 mM NaCl, pH 6.3, and the $A_{280}$ peak was collected. All column flows were at a linear velocity of 200 cm/hr.

Adventitious viruses were removed using nano filtration. The cation-exchange column eluate was passed through a 0.1 μm filter followed in series with a 30-inch cartridge membrane filter (ULTIPOR DV20; Pall Corporation, Northborough, Mass.), and the filtrate was collected.

In subsequent experiments, the PABA resin was sanitized using 0.1 M acetic acid+20% EtOH. This procedure resulted in improved stability of the resin.

Example 2

The effect of pH on the conversion of recombinant PT-1 to thrombin was studied. Experiments were carried out essentially as described in Example 1 using a 2000:1 ratio of PT-1 to immobilized Oscutarin C and a contact time of 2.5 minutes, with the pH of the activation reaction varied from 6.8 to 8.0. Within this pH range the best conversion of PT-1 to thrombin was reported at pH 7.4. At pH 6.8, the PT-1 to thrombin reaction was less efficient, resulting in lower thrombin yields. At pH 8.0 there was the trend for PT-1 to be converted to PT-2, again resulting in lower thrombin yields. See FIGS. 3-5.

A second series of experiments conducted at pH 6.0 to 7.4 showed that the thrombin yield dropped about 20% at pH 6.0 vs pH 7.4. Interestingly, in this set of four experiments where activations were done at pH 7.4, 6.8, 6.4, and 6.0, the conversion of PT-1 to thrombin was fairly constant until pH 6.0 was achieved. In addition, the resin was found to be less stable at the lower pH levels compared to higher levels.

Example 3

Activation of PT-1 was carried out essentially as described in Example 1 using varying concentrations of NaCl at pH 7.4. Increasing concentrations of NaCl were found to inhibit the activation reaction as shown in FIG. 6 (300 mM NaCl; 29.4 mS/cm), FIG. 7 (120 mM NaCl; 14.3 mS/cm), and FIG. 8 (70 mM NaCl; 8.7 mS/cm). However, some NaCl had to be included in the reaction buffer to maintain stability of PT-1 in solution. Through a series of experiments it was determined that 70 mM NaCl provided a suitable combination of PT-1 stability and activation efficiency.

Experiments were also done at 30 mM NaCl with a slight increase in product yield observed, although at some loss of stability.

Example 4

The effect on activation of residence time of PT-1 on the activator column was studied by varying the flow rate with activation conditions essentially as described in Example 1. 1.0-mL bolus volumes of PT-1 were injected over a scaled-down PTA column. Fractions were collected, quenched in a solution containing soluble benzamidine, and assayed by reverse-phase HPLC for PT-1, PT-2, and thrombin concentrations. Shorter contact times (higher flow rates) resulted in poorer conversion of PT-1 to thrombin. These studies also showed that there was only a modest drop in PT-1 activation at the end of the conversion process compared to the initial conversion measurements. A graphical representation of this data is shown in FIG. 1.

At PT-1 concentrations between 4 and 6 mg/mL, a contact time of 2.5 minutes resulted in good conversion. As shown in FIG. 10, suitable results were obtained with a 4.0 mg/mL PT-1 load (2000 mgPT-1/mL resin) and a contact time of 2.5 minutes.

Example 5

The effect of process parameters on PT-1 and PT-2 activation was studied. 20 mL each of PT-1 and PT-2 was dialyzed into 20 mM Tris, 120 mM NaCl, pH 7.4 for 17.5 hours at 2-8° C. The dialyzed proteins were then diluted to 1 mg/mL in the same buffer. The protein solutions were applied to the activator column at flow rates of 0.2-0.5 mL/min at equimolar injections. As shown in FIG. 2, the conversion rate of PT-1 to thrombin was greater than the conversion rate of PT-2. Also as shown in FIG. 2, the conversion drop-off rate as a function of contact time for PT-1 was less than for PT-2, indicating that PT-2 conversion is more influenced by contact time on the activator.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for converting prethrombin-1 to thrombin comprising:
    providing prethrombin-1 at a concentration of 0.1 mg/mL to 10 mg/mL in an aqueous solution of 30 mM to 110 mM NaCl at pH 6.4-8.0;
    providing oscutarin-C immobilized on a solid support; and
    applying the aqueous solution to the immobilized oscutarin-C so as to provide from 500 mg to 4000 mg of prethrombin-1 per mL of the solid support and a contact time between the prethrombin-1 and the oscutarin-C of from 1.8 to 3.5 minutes inclusive, whereby the prethrombin-1 is cleaved to produce thrombin, and a thrombin-containing solution is obtained.

2. The method of claim 1 further comprising:
    applying the thrombin-containing solution to a capture medium selected from the group consisting of an ion exchange chromatography medium and an affinity chromatography medium, whereby the thrombin is bound to the capture medium;
    washing the bound thrombin; and
    recovering the bound thrombin from the capture medium.

3. The method of claim 2 wherein the capture medium is an affinity chromatography medium.

4. The method of claim 3 wherein the affinity chromatography medium comprises PABA immobilized on a solid support.

5. The method of claim 2 wherein the aqueous solution of prethrombin-1 is at pH=7.4.

6. The method of claim 2 wherein the prethrombin-1 is human prethrombin-1.

7. The method of claim 1 wherein the oscutarin-C is immobilized on a cross-linked agarose matrix.

8. The method of claim 7 wherein the concentration of oscutarin-C on the matrix is 1.0 mg/mL.

9. The method of claim 1 wherein the aqueous solution of prethrombin-1 is at pH=7.4.

10. The method of claim 1 wherein the prethrombin-1 is human prethrombin-1.

11. The method of claim 1, which is carried out at a temperature of from 17° C. to 45° C.

12. The method of claim 11, which is carried out at a temperature of from 20° C. to 37° C.

13. The method of claim 11, which is carried out at a temperature of from 20° C. to 30° C.

14. The method of claim 11, which is carried out at a temperature of 25° C.

15. The method of claim 1 wherein the oscutarin-C is immobilized on the solid support at a concentration of from 0.1 to 20 mg of oscutarin-C per mL of support.

16. The method of claim 15 wherein the concentration is from 0.1 to 5.0 mg of oscutarin-C per mL of support.

17. The method of claim 1 wherein the NaCl concentration in the aqueous solution of prethrombin-1 is 70 mM.

18. A method for converting prethrombin-1 to thrombin comprising:
    providing prethrombin-1 at a concentration of 1.0 mg/mL to 10 mg/mL in an aqueous solution of 30 mM to 110 mM NaCl at pH=6.8-8.0;
    providing oscutarin-C immobilized on a solid support at a concentration of from 0.1 mg to 20 mg of oscutarin-C per mL of support; applying the prethrombin-1 to the immobilized oscutarin-C so as to provide a ratio of prethrombin-1:oscutarin-C of from 500 mg to 4000 mg of prethrombin-1 per mL of the solid support and a contact time between the prethrombin-1 and the oscutarin-C of from 1.8 to 3.5 minutes at a temperature of from 20° C.-30° C., whereby the prethrombin-1 is cleaved to produce thrombin, and a thrombin-containing solution is obtained;
    applying the thrombin-containing solution to immobilized PABA whereby the thrombin is bound to the PABA;
    washing the bound thrombin to remove impurities; and
    recovering the bound thrombin from the immobilized PABA.

19. The method of claim 18 wherein the recovering step comprises washing the immobilized PABA with NaCl and isopropanol at concentrations sufficient to elute the bound thrombin.

* * * * *

UNITED STATES PATENT AND TRADEMARK OFFICE
CERTIFICATE OF CORRECTION

PATENT NO. : 8,062,876 B2  
APPLICATION NO. : 12/097027  
DATED : November 22, 2011  
INVENTOR(S) : Mallett et al.

Page 1 of 1

It is certified that error appears in the above-identified patent and that said Letters Patent is hereby corrected as shown below:

Title Page
Please insert the following priority claim information:

--Related U.S. Application Data

(60)   Provisional application No. 60/753,914, filed on December 22, 2005.--

Column 1
Lines 4-5, please replace "claims priority to PCT/US2006/049076, filed on Dec. 21, 2006" with --is the national phase application of Application PCT/US2006/049076, filed on Dec. 21, 2006, which claims the benefit of U.S. 60/753,914, filed on Dec. 22, 2005.--

Signed and Sealed this
Twentieth Day of October, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,062,876 B2 | Page 1 of 1 |
| APPLICATION NO. | : 12/097027 | |
| DATED | : November 22, 2011 | |
| INVENTOR(S) | : Robert W. Mallet et al. | |

It is certified that error appears in the above-identified patent and that said Letters Patent is hereby corrected as shown below:

This certificate supersedes the Certificate of Correction issued October 20, 2015.
The certificate is vacated since petition to accept an unintentionally delayed priority claim under 35 U.S.C. § 120 was dismissed by the Office of Petitions. The Certificate of Correction was published in error and should not have been issued for this patent.

Signed and Sealed this
Eighth Day of December, 2015

Michelle K. Lee
*Director of the United States Patent and Trademark Office*